(12) United States Patent
Quan

(10) Patent No.: US 6,730,689 B2
(45) Date of Patent: May 4, 2004

(54) N-[4-(1H-IMIDAZOL-1-YL)-2-FLUOROPHENYL]-3-(TRIFLUOROMETHYL)-1H-PYRAZOLE-5-CARBOXAMIDES AS FACTOR XA INHIBITORS

(75) Inventor: Mimi L. Quan, Newark, DE (US)

(73) Assignee: Bristol-Myers Squibb Company, Princeton, NJ (US)

( * ) Notice: Subject to any disclaimer, the term of this patent is extended or adjusted under 35 U.S.C. 154(b) by 24 days.

(21) Appl. No.: 10/302,184

(22) Filed: Nov. 22, 2002

(65) Prior Publication Data

US 2003/0144287 A1 Jul. 31, 2003

Related U.S. Application Data

(60) Provisional application No. 60/336,972, filed on Dec. 4, 2001.

(51) Int. Cl.[7] .................. A61K 31/423; A61P 7/02; C07D 413/14
(52) U.S. Cl. ........................ 514/379; 548/241

(58) Field of Search ............................ 548/241; 514/379

(56) References Cited

U.S. PATENT DOCUMENTS

| 5,342,851 | A | 8/1994 | Sanfilippo et al. |
| 6,020,357 | A | 2/2000 | Pinto et al. |
| 6,271,237 | B1 | 8/2001 | Galemmo et al. |
| 6,339,099 | B1 * | 1/2002 | Lam et al. .................. 514/378 |
| 6,521,614 | B1 * | 2/2003 | Maduskuie, Jr. et al. ... 514/218 |

FOREIGN PATENT DOCUMENTS

| WO | WO 98/28269 | 7/1998 |

* cited by examiner

*Primary Examiner*—Robert W. Ramsuer
(74) *Attorney, Agent, or Firm*—David M. Vance; Jing S. Belfield

(57) ABSTRACT

The present application describes N-[4-(1H-imidazol-1-yl)-2-fluorophenyl]-3-(trifluoromethyl)-1H-pyrazole-5-carboxamides and derivatives thereof of, which are useful as inhibitors of factor Xa.

10 Claims, No Drawings

N-[4-(1H-IMIDAZOL-1-YL)-2-FLUOROPHENYL]-3-(TRIFLUOROMETHYL)-1H-PYRAZOLE-5-CARBOXAMIDES AS FACTOR XA INHIBITORS

CROSS-REFERENCE TO RELATED APPLICATIONS

The present application claims the priority benefit of U.S. Provisional Application No. 60/336,972, filed Dec. 4, 2001, the disclosure of which is incorporated herein by reference in its entirety.

FIELD OF THE INVENTION

This invention relates generally to novel N-[4-(1H-imidazol-1-yl)-2-fluorophenyl]-3-(trifluoromethyl)-1H-pyrazole-5-carboxamides which are inhibitors of trypsin-like serine protease enzymes, especially factor Xa, pharmaceutical compositions containing the same, and methods of using the same as anticoagulant agents for treatment and prevention of thromboembolic disorders.

BACKGROUND OF THE INVENTION

U.S. Pat. No. 5,342,851 depicts thiazole platelet aggregation inhibitors including those of the following formula:

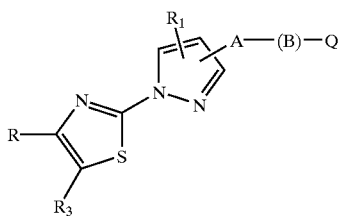

wherein A is a linker, B can be a linker or a ring, Q is a ring or an amino group, R, $R_1$, and $R_3$ are a variety of groups. This patent, however, does not exemplify or suggest compounds of the present invention.

WO00/39131 describes heterobicyclic Factor Xa inhibitors of which the following is an example formula:

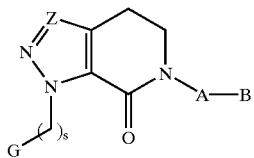

wherein Z is C or N, G is a mono- or bicyclic group, A is a cyclic moiety and B is a basic group or a cyclic moiety. Compounds specifically described in WO00/39131 are not considered to be part of the present invention.

WO98/28269, WO99/32454, U.S. Pat. No. 6,020,357, and U.S. Pat. No. 6,271,237 describe Factor Xa inhibitors of the following formula:

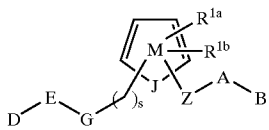

wherein ring M can be pyrazolyl, A is a ring, B can be a ring, D can be amidino, and E can be phenyl. Compounds specifically described in WO98/28269, WO99/32454, U.S. Pat. No. 6,020,357, and U.S. Pat. No. 6,271,237 are not considered to be part of the present invention.

WO98/57951 describes Factor Xa inhibitors of the following formula:

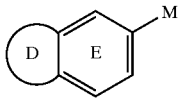

wherein ring M can be pyrazolyl and rings D—E can be amino-benzisoxazole. Compounds specifically described in WO98/57951 are not considered to be part of the present invention.

Activated factor Xa, whose major practical role is the generation of thrombin by the limited proteolysis of prothrombin, holds a central position that links the intrinsic and extrinsic activation mechanisms in the final common pathway of blood coagulation. The generation of thrombin, the final serine protease in the pathway to generate a fibrin clot, from its precursor is amplified by formation of prothrombinase complex (factor Xa, factor V, $Ca^{2+}$ and phospholipid). Since it is calculated that one molecule of factor Xa can generate 138 molecules of thrombin (Elodi, S., Varadi, K.: Optimization of conditions for the catalytic effect of the factor IXa-factor VIII Complex: Probable role of the complex in the amplification of blood coagulation. *Thromb. Res.* 1979, 15, 617–629), inhibition of factor Xa may be more efficient than inactivation of thrombin in interrupting the blood coagulation system.

Therefore, efficacious and specific inhibitors of factor Xa are needed as potentially valuable therapeutic agents for the treatment of thromboembolic disorders. It is thus desirable to discover new factor Xa inhibitors. In addition, it is also desirable to find new compounds with improved pharmacological characteristics compared with known factor Xa inhibitors. For example, it is preferred to find new compounds with improved factor Xa inhibitory activity and selectivity for factor Xa versus other serine proteases (i.e., trypsin). It is also desirable and preferable to find compounds with advantageous and improved characteristics in one or more of the following categories, but are not limited to: (a) pharmaceutical properties (e.g., solubility, permeability, and amenability to sustained release formulations); (b) dosage requirements (e.g., lower dosages and/or once-daily dosing); (c) factors which decrease blood concentration peak-to-trough characteristics (e.g., clearance and/or volume of distribution); (d) factors that increase the concentration of active drug at the receptor (e.g., protein binding, volume of distribution); (e) factors that decrease the liability for clinical drug-drug interactions (e.g., cytochrome P450 enzyme inhibition or induction); (f) factors that decrease the potential for adverse side-effects (e.g., pharmacological selectivity beyond serine proteases, potential chemical or metabolic reactivity, and limited CNS penetration); and, (g) factors that improve manufacturing costs or feasibility (e.g., difficulty of synthesis, number of chiral centers, chemical stability, and ease of handling).

SUMMARY OF THE INVENTION

Accordingly, the present invention provides novel N-[4-(1H-imidazol-1-yl)-2-fluorophenyl]-3-(trifluoromethyl)-1H-pyrazole-5-carboxamides that are useful as factor Xa inhibitors or pharmaceutically acceptable salts or prodrugs thereof.

The present invention provides pharmaceutical compositions comprising a pharmaceutically acceptable carrier and a therapeutically effective amount of at least one of the compounds of the present invention or a pharmaceutically acceptable salt or prodrug form thereof.

The present invention provides a method for treating thromboembolic disorders comprising administering to a host in need of such treatment a therapeutically effective amount of at least one of the compounds of the present invention or a pharmaceutically acceptable salt or prodrug form thereof.

The present invention provides a novel method of treating a patient in need of thromboembolic disorder treatment, comprising: administering a compound of the present invention or a pharmaceutically acceptable salt form thereof in an amount effective to treat a thromboembolic disorder.

The present invention provides a novel method, comprising: administering a compound of the present invention or a pharmaceutically acceptable salt form thereof in an amount effective to treat a thromboembolic disorder.

The present invention provides novel compounds for use in therapy.

The present invention provides the use of novel compounds for the manufacture of a medicament for the treatment of a thromboembolic disorder.

These and other objects, which will become apparent during the following detailed description, have been achieved by the inventors' discovery that the compounds of the present invention are effective factor Xa inhibitors.

DETAILED DESCRIPTION OF PREFERRED EMBODIMENTS

[1] Thus, in an embodiment, the present invention provides a novel compound of formula I:

I or a pharmaceutically acceptable salt thereof, wherein:

R is H or $C_{1-6}$ alkyl;

$R^1$ is selected from the group:
  H;
  $C_{1-6}$ alkenylene-C(O)—$C_{1-6}$ alkyl;
  C(O)—$C_{1-6}$ alkyl;
  C(O)—$C_{1-6}$ alkyl-$NR^aR^a$, wherein $R^a$ is independently H or $C_{1-6}$ alkyl;
  C(O)$CH_2CH_2CH(NR^aR^a)C(O)OR^a$, wherein $R^a$ is independently H or $C_{1-6}$ alkyl;
  C(O)-phenyl substituted with 0–2 $R^2$;
  C(O)OCH$_2$OPO$_3$H;
  C(O)OCH$_2$O—$C_{1-6}$ alkyl;
  CH$_2$OC(O)-phenyl substituted with 0–2 $R^2$;
  CH$_2$OC(O)CH$_2$-5–6 membered heterocycle consisting of carbon atoms and 1–2 heteroatoms selected from O and N, and substituted with 0–2 $R^2$; and, wherein the asterisk defines the point of attachment;

$R^2$ is selected from Cl, F, Br, I, OH, $C_{1-6}$ alkyl, $C_{1-6}$ alkyl-OH, $C_{1-6}$ alkoxy, and $C_{1-4}$ alkylene-OC(O)—$C_{1-6}$ alkyl; and, $R^3$ is selected from $C_{1-6}$ alkyl and phenyl substituted with 0–2 $R^2$.

[2] In a preferred embodiment, $R^1$ is selected from:

-continued

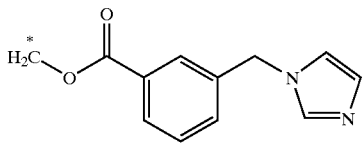

H, —CH$_2$OH, —CH$_2$OC(O)OCH$_3$, —CH$_2$OC(O) Phenyl, —C(O)CH$_3$, —C(O)CH$_2$NH$_2$, —C(O)CH$_2$CH$_2$CH(NH$_2$)C(O)OH, —C(O)OCH$_2$OPO$_3$H, —C(O)OCH$_2$OC(O)CH$_3$, and —C(CH$_3$)=CHC(O)CH$_3$, wherein the asterisk defines the point of attachment.

[3] In another preferred embodiment, the present invention provides a novel compound wherein:

R is CH$_3$; and,
R$^1$ is H.

[4] In another preferred embodiment, the present invention provides a novel compound wherein:

R is H; and,
R$^1$ is H.

[5] In another embodiment, the present invention provides a novel compound of formula II:

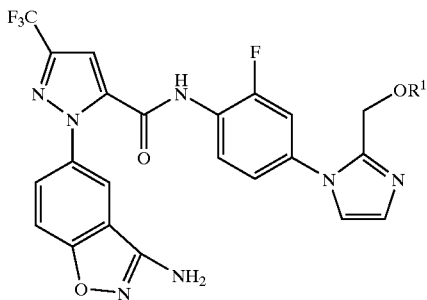

II or a pharmaceutically acceptable salt thereof, wherein:

R$^1$ is selected from the group:
 H;
 C(O)—C$_{1-6}$ alkyl;
 C(O)—C$_{1-6}$ alkyl-OH;
 C(O)O—C$_{1-6}$ alkyl;
 C(O)OCH$_2$OPO$_3$H; and,
 C(O)-phenyl substituted with 0–2 R$^4$; and, R$^4$ is selected from:
 CH$_2$NR$^a$R$^a$, wherein R$^a$ is independently H or C$_{1-6}$ alkyl;
 CH$_2$NR$^a$R$^a$(CH$_2$)$_2$NR$^a$R$^a$, wherein R$^a$ is independently H or C$_{1-6}$ alkyl;
 CH$_2$-5–6 membered heterocycle consisting of carbon atoms and 1–2 heteroatoms selected from O and N, and substituted with 0–2 R$^2$.

[6] In another preferred embodiment, R$^1$ is selected from:

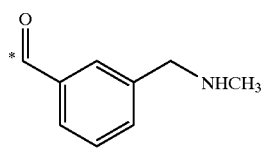

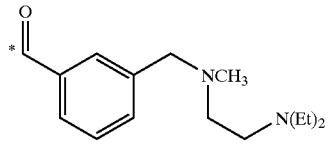

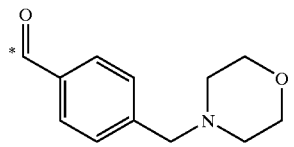

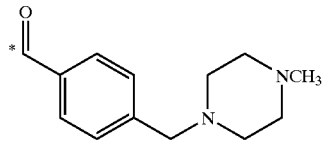

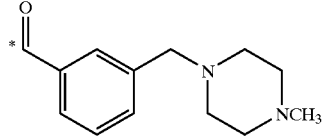

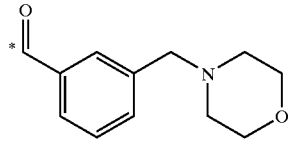

H, —C(O)CH$_2$OH, —C(O)OCH$_3$, —C(O)CH$_3$, and —C(O)OCH$_2$OPO$_3$H, wherein the asterisk defines the point of attachment.

[7] In another preferred embodiment, R$^1$ is H.

[8] In another embodiment, the present invention provides a novel compound of formula III:

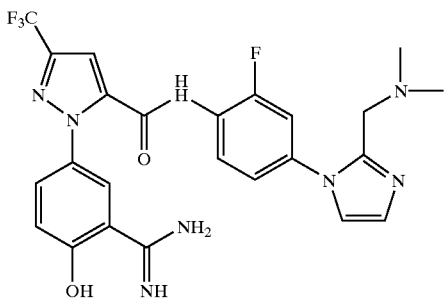

III or a pharmaceutically acceptable salt thereof.

[9] In another embodiment, the present invention provides a novel compound of formula IV:

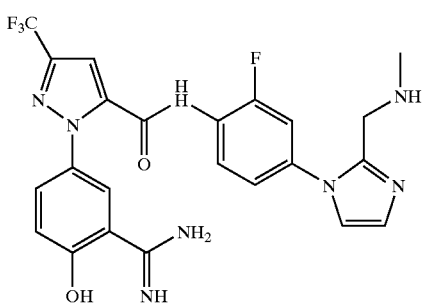

IV or a pharmaceutically acceptable salt thereof.

In another embodiment, the present invention provides novel pharmaceutical compositions, comprising: a pharmaceutically acceptable carrier and a therapeutically effective amount of a compound of the present invention or a pharmaceutically acceptable salt form thereof.

In another embodiment, the present invention provides a novel method for treating a thromboembolic disorder, comprising: administering to a patient in need thereof a therapeutically effective amount of a compound of the present invention or a pharmaceutically acceptable salt form thereof.

In another preferred embodiment, the present invention provides a novel method, wherein the thromboembolic disorder is selected from the group consisting of arterial cardiovascular thromboembolic disorders, venous cardiovascular thromboembolic disorders, and thromboembolic disorders in the chambers of the heart.

In another preferred embodiment, the present invention provides a novel method, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis.

In another embodiment, the present invention provides a novel method of treating a patient in need of thromboembolic disorder treatment, comprising: administering a compound of the present invention or a pharmaceutically acceptable salt form thereof in an amount effective to treat a thromboembolic disorder.

In another embodiment, the present invention provides a novel method, comprising: administering a compound of the present invention or a pharmaceutically acceptable salt form thereof in an amount effective to treat a thromboembolic disorder.

In another embodiment, the present invention provides a novel method for treating a thromboembolic disorder, comprising: administering to a patient in need thereof a therapeutically effective amount of a first and second therapeutic agent, wherein the first therapeutic agent is compound of the present invention or a pharmaceutically acceptable salt thereof and the second therapeutic agent is at least one agent selected from a second factor Xa inhibitor, an anti-coagulant agent, an anti-platelet agent, a thrombin inhibiting agent, a thrombolytic agent, and a fibrinolytic agent.

In another preferred embodiment, the present invention provides a novel method, wherein the second therapeutic agent is at least one agent selected from warfarin, unfractionated heparin, low molecular weight heparin, synthetic pentasaccharide, hirudin, argatrobanas, aspirin, ibuprofen, naproxen, sulindac, indomethacin, mefenamate, droxicam, diclofenac, sulfinpyrazone, piroxicam, ticlopidine, clopidogrel, tirofiban, eptifibatide, abciximab, melagatran, disulfatohirudin, tissue plasminogen activator, modified tissue plasminogen activator, anistreplase, urokinase, and streptokinase.

In another preferred embodiment, the present invention provides a novel method, wherein the second therapeutic agent is at least one anti-platelet agent.

In another preferred embodiment, the present invention provides a novel method, wherein the anti-platelet agent is aspirin and clopidogrel.

In another preferred embodiment, the present invention provides a novel method, wherein the anti-platelet agent is clopidogrel.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a novel article of manufacture, comprising:

(a) a first container;

(b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used in combination with a second therapeutic agent to treat a thromboembolic disorder.

In another preferred embodiment, the present invention provides a novel article of manufacture, further comprising:

(d) a second container;

wherein components (a) and (b) are located within the second container and component (c) is located within or outside of the second container.

In another embodiment, the present invention provides a compound of the present invention for use in therapy.

In another embodiment, the present invention provides the use of a compound of the present invention for the manufacture of a medicament for the treatment of a thromboembolic disorder.

The present invention may be embodied in other specific forms without departing from the spirit or essential attributes thereof. This invention encompasses all combinations of preferred aspects of the invention noted herein. It is understood that any and all embodiments of the present invention may be taken in conjunction with any other embodiment or embodiments to describe additional more preferred embodiments. It is also to be understood that each individual element of the preferred embodiments is intended to be taken individually as its own independent preferred embodiment. Furthermore, any element of an embodiment is meant to be combined with any and all other elements from any embodiment to describe an additional embodiment.

DEFINITIONS

Geometric isomers of olefins, C=N double bonds, and the like can be present in the compounds described herein, and all such stable isomers are contemplated in the present invention. Cis and trans geometric isomers of the compounds of the present invention are described and may be isolated as a mixture of isomers or as separated isomeric forms. All geometric isomeric forms of a structure are intended, unless the specific isomeric form is indicated.

The term "substituted," as used herein, means that any one or more hydrogens on the designated atom is replaced with a selection from the indicated group, provided that the designated atom's normal valency is not exceeded, and that the substitution results in a stable compound. When a substituent is keto (i.e., =O), then 2 hydrogens on the atom are replaced. Keto substituents are not present on aromatic moieties.

The present invention is intended to include all isotopes of atoms occurring in the present compounds. Isotopes include those atoms having the same atomic number but different mass numbers. By way of general example and without limitation, isotopes of hydrogen include tritium and deuterium. Isotopes of carbon include C-13 and C-14.

The present invention is also intended to include all stable oxides of thiol and amino groups, even when not specifically written. When an amino group is listed as a substituent, the N-oxide derivative of the amino group is also included as a substituent. When a thiol group is present, the S-oxide and S,S-dioxide derivatives are also included.

When any variable (e.g., $R^6$) occurs more than one time in any constituent or formula for a compound, its definition at each occurrence is independent of its definition at every other occurrence. Thus, for example, if a group is shown to be substituted with 0–2 $R^6$, then said group may optionally be substituted with up to two $R^6$ groups and $R^6$ at each occurrence is selected independently from the definition of $R^6$. Also, combinations of substituents and/or variables are permissible only if such combinations result in stable compounds.

When a bond to a substituent is shown to cross a bond connecting two atoms in a ring, then such substituent may be bonded to any atom on the ring. When a substituent is listed without indicating the atom via which such substituent is bonded to the rest of the compound of a given formula, then such substituent may be bonded via any atom in such substituent. Combinations of substituents and/or variables are permissible only if such combinations result in stable compounds.

As used herein, "alkyl" is intended to include both branched and straight-chain saturated aliphatic hydrocarbon groups having the specified number of carbon atoms. $C_{1-10}$ alkyl, is intended to include $C_1$, $C_2$, $C_3$, $C_4$, $C_5$, $C_6$, $C_7$, $C_8$, $C_9$, and $C_{10}$ alkyl groups. Examples of alkyl include, but are not limited to, methyl, ethyl, n-propyl, i-propyl, n-butyl, s-butyl, t-butyl, n-pentyl, and s-pentyl. "Haloalkyl" is intended to include both branched and straight-chain saturated aliphatic hydrocarbon groups having the specified number of carbon atoms, substituted with 1 or more halogen (for example —$C_vF_w$ where v=1 to 3 and w=1 to (2v+1)). Examples of haloalkyl include, but are not limited to, trifluoromethyl, trichloromethyl, pentafluoroethyl, and pentachloroethyl. "Alkoxy" represents an alkyl group as defined above with the indicated number of carbon atoms attached through an oxygen bridge. $C_{1-10}$ alkoxy, is intended to include $C_1$, $C_2$, $C_3$, $C_4$, $C_5$, $C_6$, $C_7$, $C_8$, $C_9$, and $C_{10}$ alkoxy groups. Examples of alkoxy include, but are not limited to, methoxy, ethoxy, n-propoxy, i-propoxy, n-butoxy, s-butoxy, t-butoxy, n-pentoxy, and s-pentoxy. "Cycloalkyl" is intended to include saturated ring groups, such as cyclopropyl, cyclobutyl, or cyclopentyl. $C_{3-7}$ cycloalkyl is intended to include $C_3$, $C_4$, $C_5$, $C_6$, and $C_7$ cycloalkyl groups. Alkenyl" is intended to include hydrocarbon chains of either straight or branched configuration and one or more unsaturated carbon-carbon bonds that may occur in any stable point along the chain, such as ethenyl and propenyl. $C_{2-10}$ alkenyl is intended to include $C_2$, $C_3$, $C_4$, $C_5$, $C_6$, $C_7$, $C_8$, $C_9$, and $C_{10}$ alkenyl groups. "Alkynyl" is intended to include hydrocarbon chains of either straight or branched configuration and one or more triple carbon-carbon bonds that may occur in any stable point along the chain, such as ethynyl and propynyl. $C_{2-10}$ Alkynyl is intended to include $C_2$, $C_3$, $C_4$, $C_5$, $C_6$, $C_7$, $C_8$, $C_9$, and $C_{10}$ alkynyl groups. "Halo" or "halogen" as used herein refers to fluoro, chloro, bromo, and iodo; and "counterion" is used to represent a small, negatively charged species such as chloride, bromide, hydroxide, acetate, and sulfate.

As used herein, "carbocycle" or "carbocyclic residue" is intended to mean any stable 3, 4, 5, 6, or 7-membered monocyclic or bicyclic or 7, 8, 9, 10, 11, 12, or 13-membered bicyclic or tricyclic, any of which may be saturated, partially unsaturated, or aromatic. Examples of such carbocycles include, but are not limited to, cyclopropyl, cyclobutyl, cyclopentyl, cyclohexyl, cycloheptyl, adamantyl, cyclooctyl, [3.3.0]bicyclooctane, [4.3.0]bicyclononane, [4.4.0]bicyclodecane, [2.2.2] bicyclooctane, fluorenyl, phenyl, naphthyl, indanyl, adamantyl, and tetrahydronaphthyl.

As used herein, the term "heterocycle" or "heterocyclic system" is intended to mean a stable 5, 6, or 7-membered monocyclic or bicyclic or 7, 8, 9, 10, 11, or 12-membered bicyclic or tricyclic heterocyclic ring which is saturated, partially unsaturated or unsaturated (aromatic), and which consists of carbon atoms and 1, 2, 3, or 4 heteroatoms independently selected from the group consisting of N, O, and S and including any bicyclic group in which any of the above-defined heterocyclic rings is fused to a benzene ring. The nitrogen and sulfur heteroatoms may optionally be oxidized. The nitrogen atom may be substituted or unsubstituted (i.e., N or NR wherein R is H or another substituent, if defined). The heterocyclic ring may be attached to its pendant group at any heteroatom or carbon atom that results in a stable structure. The heterocyclic rings described herein may be substituted on carbon or on a nitrogen atom if the resulting compound is stable. A nitrogen in the heterocycle may optionally be quaternized. It is preferred that when the total number of S and O atoms in the heterocycle exceeds 1, then these heteroatoms are not adjacent to one another. It is preferred that the total number of S and O atoms in the heterocycle is not more than 1. As used herein, the term "aromatic heterocyclic system" or "heteroaryl" is intended to mean a stable 5, 6, or 7-membered monocyclic or bicyclic or 7, 8, 9, or 10-membered bicyclic heterocyclic aromatic ring which consists of carbon atoms and 1, 2, 3, or 4 heteroatoms independently selected from the group consisting of N, O, and S. It is to be noted that total number of S and O atoms in the aromatic heterocycle is not more than 1.

Examples of heterocycles include, but are not limited to, acridinyl, azocinyl, benzimidazolyl, benzofuranyl, benzothiofuranyl, benzothiophenyl, benzoxazolyl, benzoxazolinyl, benzthiazolyl, benztriazolyl, benztetrazolyl, benzisoxazolyl, benzisothiazolyl, benzimidazolinyl, carbazolyl, 4aH-carbazolyl, carbolinyl, chromanyl, chromenyl, cinnolinyl, decahydroquinolinyl, 2H,6H-1,5,2-dithiazinyl, dihydrofuro[2,3-b] tetrahydrofuran, furanyl, furazanyl, imidazolidinyl, imidazolinyl, imidazolyl, 1H-indazolyl, indolenyl, indolinyl, indolizinyl, indolyl, 3H-indolyl, isatinoyl, isobenzofuranyl, isochromanyl, isoindazolyl, isoindolinyl, isoindolyl, isoquinolinyl, isothiazolyl, isoxazolyl, methylenedioxyphenyl, morpholinyl, naphthyridinyl, octahydroisoquinolinyl, oxadiazolyl, 1,2,3-oxadiazolyl, 1,2,4-oxadiazolyl, 1,2,5-oxadiazolyl, 1,3,4-oxadiazolyl, oxazolidinyl, oxazolyl, oxindolyl, pyrimidinyl, phenanthridinyl, phenanthrolinyl, phenazinyl, phenothiazinyl, phenoxathinyl, phenoxazinyl, phthalazinyl, piperazinyl, piperidinyl, piperidonyl, 4-piperidonyl, piperonyl, pteridinyl, purinyl, pyranyl, pyrazinyl, pyrazolidinyl, pyrazolinyl, pyrazolyl, pyridazinyl, pyridooxazole, pyridoimidazole, pyridothiazole, pyridinyl, pyridyl, pyrimidinyl, pyrrolidinyl, pyrrolinyl, 2H-pyrrolyl, pyrrolyl, quinazolinyl, quinolinyl, 4H-quinolizinyl, quinoxalinyl, quinuclidinyl, tetrahydrofuranyl, tetrahydroisoquinolinyl, tetrahydroquinolinyl, tetrazolyl, 6H-1,2,5-thiadiazinyl, 1,2,3-thiadiazolyl, 1,2,4-thiadiazolyl, 1,2,5-thiadiazolyl, 1,3,4-thiadiazolyl, thianthrenyl, thiazolyl, thienyl, thienothiazolyl, thienooxazolyl, thienoimidazolyl, thiophenyl, triazinyl, 1,2,3-triazolyl, 1,2,4-triazolyl, 1,2,5-triazolyl, 1,3,4-triazolyl, and xanthenyl. Also included are fused ring and spiro compounds containing, for example, the above heterocycles.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, ethane sulfonic, fumaric, glucoheptonic, gluconic, glutamic, glycolic, glycollyarsanilic, hexylresorcinic, hydrabamic, hydrobromic, hydrochloric, hydroiodide, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, and toluene sulfonic.

The pharmaceutically acceptable salts of the present invention can be synthesized from the parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile are preferred. Lists of suitable salts are found in *Remington's Pharmaceutical Sciences*, 18th ed., Mack Publishing Company, Easton, Pa., 1990, p 1445, the disclosure of which is hereby incorporated by reference.

"Prodrugs" are intended to include any covalently bonded carriers that release the active parent drug according to the present invention in vivo when such prodrug is administered to a mammalian subject. Prodrugs of a compound of the present invention are prepared by modifying functional groups present in the compound in such a way that the modifications are cleaved, either in routine manipulation or in vivo, to the parent compound. Prodrugs include compounds of the present invention wherein a hydroxy, amino, or sulfhydryl group is bonded to any group that, when the prodrug or compound of the present invention is administered to a mammalian subject, cleaves to form a free hydroxyl, free amino, or free sulfhydryl group, respectively. Examples of prodrugs include, but are not limited to, acetate, formate and benzoate derivatives of alcohol and amine functional groups in the compounds of the present invention, and the like.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

"Stable compound" and "stable structure" are meant to indicate a compound that is sufficiently robust to survive isolation to a useful degree of purity from a reaction mixture, and formulation into an efficacious therapeutic agent.

Other features of the invention will become apparent in the course of the following descriptions of exemplary embodiments which are given for illustration of the invention and are not intended to be limiting thereof.

EXAMPLES

Preparative Example A 1-(3-cyano-4-fluorophenyl)-3-(trifluoromethyl)-1H-pyrazole-5-carboxylic acid Method A:

To a suspension of 3-cyano-4-fluoro-phenylhydrazine tin chloride (20 g, 53.6 mmol) in ethanol (150 mL) was added 1,1,1-trifluoro-2,4-pentanedione (8.18 g, 53.6 mmol). The reaction was brought to reflux overnight. The next day the ethanol was evaporated and the residue partitioned between ethyl acetate and HCl (1 N). The aqueous phase was extracted with ethyl acetate (4×20 mL). The organic phase is washed with water, brine, dried over sodium sulfate, filtered and concentrated. Flash chromatography gave 1-(3-cyano-4-fluoro-phenyl)-3-trifluoromethyl-5-methylpyrazole (8 g, 56% yield) as pure compound: MS (CI): 270 (M+H)$^+$ (100%).

To a solution of 1-(3-cyano-4-fluoro-phenyl)-3-trifluoromethyl-5-methylpyrazole (4.0 g, 14.9 mmol) in CCl$_{14}$ (75 mL) was added NBS (5.3 g, 29.7 mmol) and benzylperoxide (0.2 g, 1.49 mmol). The reaction was brought to reflux overnight. The next day the CCl$_4$ was evaporated and the residue was partitioned between ethyl acetate and sodium bicarbonate (sat.). The organic phase was washed with water, brine, dried over sodium sulfate, filtered and concentrated. Flash chromatography gave 1-(3-cyano-4-fluoro-phenyl)-3-trifluoromethyl-5-bromomethylpyrazole (2.6 g, 50% yield) as pure compound: MS (CI): 348 (M+H)$^+$ (100%).

To a solution of 1-(3-cyano-4-fluoro-phenyl)-3-trifluoromethyl-5-bromomethylpyrazole (0.6 g, 1.72 mmol) in DMSO (10 mL) was added copper (I) oxide (0.52 g, 3.62 mmol) and water (3 mL). The reaction was stirred at 60° C. overnight. The next day the reaction mixture was filtered through Celite®. The filtrate was partitioned between ethyl acetate and water. The organic was washed three times with water, brine, dried over sodium sulfate, filtered and concentrated to give 1-(3-cyano-4-fluoro-phenyl)-3- trifluoromethyl-5-hydroxymethyl pyrazole (0.45 g, 92% yield) as pure compound: MS (CI): 286 (M+H)+ (100%).

To a solution of 1-(3-cyano-4-fluoro-phenyl)-3-trifluoromethyl-5-hydroxymethylpyrazole (0.45 g, 1.58 mmol) in acetonitrile (10 mL) was added catalytic amount of ruthenium chloride at 0° C. followed by addition of a solution of sodium periodate (0.71 g, 3.32 mmol) in water. The reaction was stirred at 0° C. to room temperature overnight. The next day the acetonitrile was evaporated and the residue was partitioned between ethyl acetate and water, washed with brine, dried over sodium sulfate, filtered and concentrated to give 1-(3-cyano-4-fluoro-phenyl)-3-trifluoromethyl-5-hydroxycarbonylpyrazole (0.27 g, 57% yield) as pure compound: MS (ES−): 298 (M—H)− (40%).
Method B:

To a suspension of 3-cyano-4-fluoro-phenylhyrazine tin chloride (17 g, 50 mmol) in acetic acid (200 mL) was added 4,4,4-trifluoro-1-(2-furyl)-2,4-butanedione (10.3 g, 50 mmol). The reaction was brought to reflux overnight. The next day the acetic acid was evaporated and the residue was partitioned between ethyl acetate and water. The organic layer was washed with HCl (1N), water and brine, dried over sodium sulfate, filtered and concentrated, flash chromatography to give 1-(3-cyano-4-fluoro-phenyl)-3-trifluoromethyl-5-(2-furyl) pyrazole (7.0 g, 44% yield) as pure compound. MS (CI): 322 (M+H)+ (100%).

To a solution of 1-(3-cyano-4-fluoro-phenyl)-3-trifluoromethyl-5-(2-furyl)pyrazole (4.0 g, 12.5 mmol) in acetonitrile (30 mL) was added carbon tetrachloride (30 mL), ruthenium chloride (0.4 g) and a solution of sodium periodate (11.9 g, 56.1 mmol) in water (45 mL). The reaction is stirred at room temperature overnight. The next day the reaction mixture was filtered through Celite®. The filtrate was concentrated and partitioned between ethyl acetate and HCl (1N). The organic phase was washed with water, dried over sodium sulfate, filtered and concentrated to give the title compound as pure compound. MS (ES−): 298 (M—H)− (40%).

Example 1

N-[4-(2-{[Methylamino]methyl}-1H-imidazol-1-yl)-2-fluorophenyl]-1-(3-amino-1,2-benzisoxazol-5-yl)-3-(trifluoromethyl)-1H-pyrazole-5-carboxamide, bis (Trifluoroacetic Acid) Salt

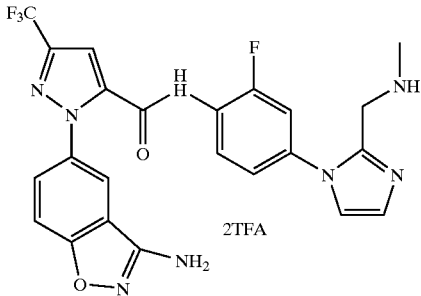

Part A: Preparation Benzyl 1H-Imidazol-2-ylmethyl (methyl)-carbamate

2-Imidazolecarboxyaldehyde (5.0 g, 52.0 mmol) was suspended in 200 mL of methanol. Methylamine (20 mL of 33% solution in methanol) was added. After stirred for 15 minutes, NaBH4 (3.95 g, 0.10 mol) was added portion-wise. The reaction mixture was then heated at 50° C. for 2 h under N2. The solvent was removed. The solid was washed with CH2Cl2 and filtered. The CH2Cl2 solution was dried over MgSO4, concentrated, and dried under vacuum to give the methylamine as a yellow oil. This oil was dissolved in a 1:1 solution of CH2Cl2 and THF. To it was added Et3N (7.94 mL, 57.0 mmol) and benzylchloroformate (7.4 mL, 52.0 mmol). The mixture was stirred at room temperature under N2 for 1 h. The solvent was removed and the residue was partitioned between EtOAc and H2O. The EtOAc layer was washed with brine, dried over MgSO4, and concentrated. The mixture was refluxed with 15 mL of TFA for 30 minutes to convert most of the bis-acylated byproduct to the desired product. The TFA was removed. It was dissolved in EtOAc and washed with saturated aqueous NaHCO3 and brine. The mixture was dried over MgSO4, concentrated, and chromatographed with 1:1 EtOAc/hexane to give 6.56 g off-white solid (51.4% yield). MS (AP+): 246.3, (M+H)+. 1H NMR (CDCl3):δ 7.35 (s, 6H), 6.90 (s, 1H), 5.14 (s, 2H), 4.48 (s, 2H), 3.00 (s, 3H)

Part B: Preparation of Benzyl {1-[4-({[1-(3-Cyano-4-fluorophenyl)-3-(trifluoromethyl)-1H-pyrazol-5-yl]carbonyl}amino)-3-fluorophenyl]-1H-imidazol-2-yl}methyl(methyl)carbamate Benzyl 1H-imidazol-2-ylmethyl(methyl)carbamate from Part A (3.60 g, 14.69 mmol), 2-fluoro-4-iodoaniline (3.50 g, 14.69 mmol), K2CO3 (2.23 g, 16.16 mmol), 1,10-phenanthroline (0.13 g, 0.73 mmol), CuI (0.14 g, 0.73 mmol), and DMSO (60 mL) were added together and degassed. The mixture was then heated at 130° C. under N2 for 12 h. The mixture was cooled, 14% aqueous NH4OH (200 mL) and EtOAC (200 mL) were added. The mixture was filtered through Celite® and washed with EtOAc. The filtrate was extracted with EtOAc, the combined organic solution was washed with brine, and dried over MgSO4. It was concentrated and purified by chromatography on silica gel with 50–100% hexane in EtOAc to give 3.46 g of the desired product (67%). MS (ES+): 355.2, (M+H)+.

Part C: Preparation of Benzyl {1-[4-({[1-(3-Cyano-4-fluorophenyl)-3-(trifluoromethyl)-1H-pyrazol-5-yl]carbonyl}amino)-3-fluorophenyl]-1H-imidazol-2-yl}methyl(methyl)carbamate 1-(3-Cyano-4-fluorophenyl)-3-(trifluoromethyl)-1H-pyrazole-5-carboxylic acid prepared as described in Example A (1.00 g, 3.34 mmol) was stirred in 20 mL of CH2Cl2 at room temperature under N2. Oxalyl chloride (0.43 mL, 5.01 mmol) was added, followed by a few drops of DMF. The mixture was stirred for 2 h. The solvent was removed and the resulting solid was dried under vacuum. This solid was then dissolved in 50 mL of CH2Cl2, benzyl {1-[4-({[1-(3-cyano-4-fluorophenyl)-3-(trifluoromethyl)-1H-pyrazol-5-yl]carbonyl}amino)-3-fluorophenyl]-1H-imidazol-2-yl}methyl(methyl)carbamate from Part B (1.32 g, 3.34 mmol) was added, followed by DMAP (1.02 g, 8.35 mmol). The mixture was stirred at room temperature under N2 for 12 h. It was diluted with CH2Cl2, washed with water and brine, dried over MgSO4, and concentrated. The crude product was purified by chromatography on silica gel with 50–100% hexane in EtOAc to give 1.10 g of the desired product (52%). MS (ES+): 636.1, (M+H)+.

Part D: Preparation of N-[4-(2-{[(Methyl)amino]methyl}-1H-imidazol-1-yl)-2-fluorophenyl]-1-(3-amino-1,2-benzisoxazol-5-yl)-3-(trifluoromethyl)-1H-pyrazole-5-carboxamide Acetohydroxamic acid (0.40 g, 5.34 mmol) was dissolved in 10 mL of DMF. K2CO3 (0.98 g, 7.12 mmol) was added, followed by 1 mL of water. The mixture was stirred at room temperature under N2 for 30 minutes and a solution of benzyl {1-[4-({[1-(3-cyano-4-fluorophenyl)-3-(trifluoromethyl)-1H-pyrazol-5-yl]carbonyl}amino)-3-fluorophenyl]-1H-imidazol-2-yl}methyl(methyl)carbamate from Part C (1.13 g, 1.78 mmol) in 10 mL of DMF was added. The resulting mixture was stirred at room temperature under N2 for 12 h. Water was added to the reaction mixture. The precipitate formed was filtered and dried. MS (ES+): 647.1, (M—H)−.

The above solid was then refluxed with 20 mL of TFA under N₂ for 30 minute. The TFA was removed. The residue was purified by reverse phase HPLC (C18 reverse phase column, eluted with a H₂O/CH₃CN gradient with 0.05% TFA) to give 0.61 g of the desired product as the bisTFA salt. MS (ES⁺): 515.0, (M+H)⁺. ¹H NMR (DMSO-d₆): δ 10.81 (s, 1H), 9.18 (bs, 2H), 8.10 (d, 1H), 7.80 (t, 1H), 7.73 (s, 1H), 7.70 (d, 1H), 7.67 (d, 1H), 7.58 (m, 4H), 7.35 (d, 1H), 7.19 (d, 1H), 6.62 (bs, 1H), 4.28 (bs, 2H), 2.63 (bs, 3H).

Example 2 of N-[4-(2-[Methylaminomethyl]-1H-imidazol-1-yl)-2-fluorophenyl]-1-(3-amidino-4-hydroxyphenyl)-3-(trifluoromethyl)-1H-pyrazole-5-carboxamide, bis (Trifluoroacetic Acid) Salt

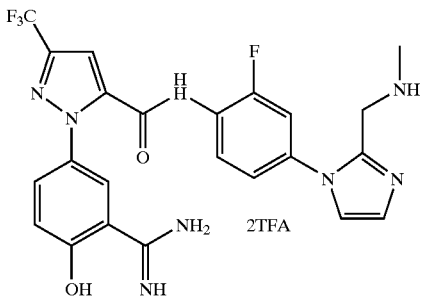

N-[4-(2-{[methylamino]methyl}-1H-imidazol-1-yl)-2-fluorophenyl]-1-(3-amino-1,2-benzisoxazol-5-yl)-3-(trifluoromethyl)-1H-pyrazole-5-carboxamide, bis (trifluoroacetic acid) salt from Example 1 (100 mg) was hydrogenated with 10% Pd/C (10 mg) and methanol (20 mL) at 35 psi for 30 minutes. The mixture was filtered through celite, concentrated, and dried to give 58 mg of the desired product as the bisTFA salt. ¹H NMR (MeOH-d₄) δ 7.93 (t, 1H), 7.81 (d, 1H), 7.64 (dd, 1H), 7.40 (m, 3H) 7.30 (d, 1H), 7.28 (s, 1H), 7.12 (d, 1H), 4.29 (s, 2H),2.74 (s, 3H), 2.01 (s, 2H). MS (ES⁺) 517.3 (M+H).

Example 3

N-[4-(2-[Hydroxymethyl]-1H-imidazol-1-yl)-2-fluorophenyl]-1-(3-amino-1,2-benzisoxazol-5-yl)-3-(trifluoromethyl)-1H-pyrazole-5-carboxamide, Trifluoroacetic Acid Salt

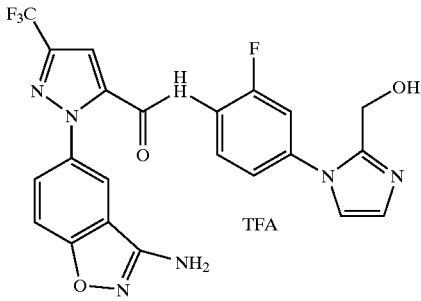

Part A: Preparation 2-Hydroxymethyl-1H-imidazole

2-Imidazolecarboxyaldehyde (5.0 g, 52.0 mmol) was suspended in 200 mL of methanol. NaBH₄ (3.95 g, 0.10 mol) was added portion-wise. The reaction mixture was stirred at room temperature for 1 h under N₂. It was quenched with 10 mL of brine. The solvent was removed. The solid was washed with 5% MeOH in CH₂Cl₂. The inorganic solid was filtered off. The filtrate was concentrated and chromatographed with 5% MeOH in CH₂Cl₂ to give 2.32 g off-white solid (45.2% yield). ¹H NMR (DMSO-d₆): δ 6.86 (s, 2H), 4.40 (s, 2H).

Part B: Preparation of 1-(4-Amino-3-fluorophenyl)-2-hydroxymethylimidazole

2-Hydroxymethyl-1H-imidazol from Part A (2.30 g, 23.47 mmol), 2-fluoro-4-iodoaniline (5.56 g, 23.47 mmol), K₂CO₃ (1.56 g, 25.82 mmol), 1,10-phenanthroline (0.42 g, 2.35 mmol), CuI (0.45 g, 2.35 mmol), and DMSO (50 mL) were added together and degassed. The mixture was then heated at 130° C. under N₂ for 12 h. The mixture was cooled, 14% aqueous NH₄OH (200 mL) and EtOAC (200 mL) were added. The mixture was filtered through Celite® and washed with EtOAc. The filtrate was extracted with EtOAc, the combined organic solution was washed with brine, and dried over MgSO₄. It was concentrated and purified by chromatography on silica gel with 5% MeOH in CH₂Cl₂ to give 0.48 g of the desired product (10%). MS (ES⁺): 208.2, (M+H)⁺. ¹H NMR (DMSO-d₆): δ 7.27 (m, 2H), 7.06 (dd, 1H), 6.94 (s, 1H), 6.83 (t, 1H), 5.41 (s, 2H), 5.34 (t, 1H), 4.36 (d, 2H).

Part C: Preparation of 1-(4-Amino-3-fluorophenyl)-2-(t-butyldimethylsilyloxymethyl)imidazole 1-(4-Amino-3-fluorophenyl)-2-hydroxymethylimidazole (0.48 g, 2.32 mmol), TBDMSCl (0.52 g, 3.48 mmol), and Et₃N (0.65 mL, 4.64 mmol) were dissolved in 20 mL of DMF. The mixture was stirred at room temperature under N₂ for 12 h. It was diluted with water and extracted with EtOAc, the combined organic solution was washed with brine, and dried over MgSO₄. It was concentrated and purified by chromatography on silica gel with 5% MeOH in CH₂Cl₂ to give 0.50 g of the desired product (67%). ¹H NMR (CDCl₃): δ 7.20 (d, 1H), 7.02 (m, 3H), 6.78 (t, 1H), 4.56 (s, 2H), 3.84 (bs, 2H), 0.82 (sd, 9H), 0.00 (s, 6H).

Part D: Preparation of N-[4-[(2-t-Butyldimethylsilyloxymethyl)-1H-imidazol-1-yl]-2-fluorophenyl]-1-(3-amino-1,2-benzisoxazol-5-yl)-3-(trifluoromethyl)-1H-pyrazole-5-carboxamide 1-(3-Cyano-4-fluorophenyl)-3-(trifluoromethyl)-1H-pyrazole-5-carboxylic acid from Example A (0.45 g, 1.50 mmol) was stirred in 20 mL of CH₂Cl₂ at room temperature under N₂. Oxalyl chloride (0.20 mL, 2.25 mmol) was added, followed by a few drops of DMF. The mixture was stirred for 2 h. The solvent was removed and the resulting solid was dried under vacuum. This solid was then dissolved in 20 mL of CH₂Cl₂, 1-(4-amino-3-fluorophenyl)-2-(t-butyldimethylsilyloxymethyl)imidazole from Part C (0.48 g, 1.50 mmol) was added, followed by DMAP (0.50 g, 4.25 mmol). The mixture was stirred at room temperature under N₂ for 12 h. It was diluted with CH₂Cl₂, washed with water and brine, dried over MgSO₄, and concentrated. The crude product was purified by chromatography on silica gel with 50% hexane in EtOAc to give 0.48 g of the desired product (53%). MS (ES⁺): 603.31, (M+H)⁺. ¹H NMR (CDCl₃): δ 8.54 (s, 1H), 8.18 (t, 1H), 7.78 (m, 2H), 7.50, 4.56 (s, 2H), 3.84 (bs, 2H), 0.82 (sd, 9H), 0.00 (s, 6H).

Part E: Preparation of N-[4-(2-[Hydroxymethyl]-1H-imidazol-1-yl)-2-fluorophenyl]-1-(3-amino-1,2-benzisoxazol-5-yl)-3-(trifluoromethyl)-1H-pyrazole-5-carboxamide Acetohydroxamic acid (0.18 g, 1.80 mmol) was dissolved in 5 mL of DMF. K₂CO₃ (0.44 g, 3.20 mmol) was added, followed by a few drops of water. The mixture was stirred at room temperature under N₂ for 30 minutes and a solution of the product from Part D (0.48 g, 0.80 mmol) was added. The resulting mixture was stirred at room temperature under N₂ for 12 h. Water was added to the reaction mixture. The precipitate formed was filtered and dried. MS (ES⁺): 616.3, (M+H)⁺. The above solid was dissolved in 20 mL of THF. Tetrabutylammonium fluoride (1.66 mL of 1M solution) was added and the mixture was stirred at room temperature under N₂ for 1 h. The THF was removed. The residue was partitioned between EtOAc and water. The organic solution was washed with water and brine, dried over MgSO₄, and concentrated to give 0.36 g of a light yellow solid (90%). This solid was about 95% pure and was taken into the next step without further purification. A small amount was purified by reverse phase HPLC (C18 reverse phase column, eluted with a H₂O/CH₃CN gradient with 0.05% TFA) to give the desired product as the TFA salt. MS (ES⁺): 502.2, (M+H)⁺. ¹H NMR (DMSO-d₆): δ 10.86 (s, 1H), 8.10 (d, 1H) 7.90 (m, 2H), 7.70 (m, 4H),), 7.58 (d, 1H), 7.50 (d, 1H), 6.62 (bs, 1H), 4.68 (s, 2H)

Example 4

N-[4-(2-[Aminomethyl]-1H-imidazol-1-yl)-2-fluorophenyl]-1-(3-amino-1,2-benzisoxazol-5-yl)-3-(trifluoromethyl)-1H-pyrazole-5-carboxamide, bis (Trifluoroacetic Acid) Salt

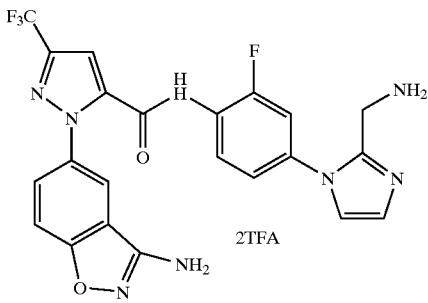

N-[4-(2-[hydroxymethyl]-1H-imidazol-1-yl)-2-fluorophenyl]-1-(3-amino-1,2-benzisoxazol-5-yl)-3-(trifluoromethyl)-1H-pyrazole-5-carboxamide From Example 3 (0.21 g, 0.42 mmol) was dissolved in 20 mL of CH₂Cl₂. PBr3 (0.18 mL, 1.76 mmol) was added. The mixture was stirred at room temperature under N₂ for 12 h. It was quenched with water and extracted with CHCl₃. The organic solution was washed with water and brine, dried over MgSO₄, and concentrated to give 0.18 g of the desired bromide. MS (ES⁺): 567.3, (M+H)⁺.

The bromide was dissolved in 5 mL of DMF and NaN₃ (62.0 mg, 1.26 mml) was added. The mixture was heated at 50° C. under N₂ for 2 h. The reaction mixture was cooled and water was added. It was extracted with EtOAc. The organic solution was washed with brine, dried over MgSO₄, and concentrated to give 0.08 g of the desired azide as a colorless oil. MS (ES⁺): 529.4, (M+H)⁺.

The above oil was refluxed with SnCl₂ (240 mg) in 10 mL of MeOH for 1 h. It was cooled, quenched with saturated, filtered through Celite®, and washed with EtOAc. The filtrate was concentrated and purified by reverse phase HPLC (C18 reverse phase column, eluted with a H₂O/CH₃CN gradient with 0.05% TFA) to give the desired product as the TFA salt. MS (ES⁺): 501.4, (M+H)⁺. ¹H NMR (DMSO-d₆): δ 10.80 (s, 1H), 8.38 (bs, 2H), 8.05 (s, 1H), 7.76 (t, 1H), 7.68–7.50 (m, 5H),), 7.32 (d, 1H), 7.16 (s, 1H), 4.10 (s, 2H).

Example 5

N-[4-(2-[Dimethylaminomethyl]-1H-imidazol-1-yl)-2-fluorophenyl]-1-(3-amidino-4-hydroxyphenyl)-3-(trifluoromethyl)-1H-pyrazole-5-carboxamide

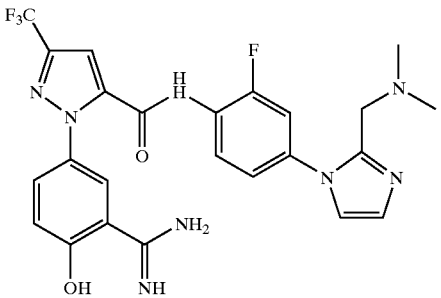

Part A: Preparation of 2-dimethylaminomethylimidazole

To a suspension of 2-imidazolecarboxaldehyde (50 g, 0.52 mol) in MeOH (400 mL) was added a solution of dimethylamine (40% aq., 400 mL) at room temperature. The mixture was stirred at RT under N₂ for 2 h. Solid sodium borohydride (50 g, 1.32 mol) was cautiously added portionwise while cooling with an ice-bath. After the addition was completed, the reaction was heated to 56° C. for 3 h and allowed to cool to rt. The reaction was quenched with brine, extracted with CH₂Cl₂. The CH₂Cl₂ extracts were washed with brine, dried (MgSO₄), filtered, and concentrated in vacuo to give the desired product (43.8 g) as a waxy solid in 67% yield: ¹H NMR (CDCl₃) δ 6.98 (s, 2H); 3.62 (s, 2H); 2.30 (s, 6H)

Part B: Preparation of 2-Fluoro-4-[(2-dimethylaminomethyl)-imidazol-1-yl]-aniline To a 500 mL RBF equipped with a reflux condenser and an internal temperature probe was added 2-fluoro-4-iodoaniline (9.8 g, 0.0415 mol), K₂CO₃ (11.5 g, 0.083 mol, 2 eq), Cu(I)I (1.58 g, 0.0083 mol, 0.2 eq), 2-dimethylaminomethyl-imidazole (7.8 g, 0.023 mol, 1.5 eq), and DMSO (300 mL). The reaction contents were heated to 120° C. overnight. After cooling to rt, the reaction was partitioned between brine (1L) and EtOAc (2×500 mL). The aqueous layer was extracted with additional CHCl₃ (500 mL) and kept separate. The organic extracts were washed with brine, dried (MgSO₄), filtered and concentrated together. The crude black oil (37 g, with DMSO) was purified by chromatography on silica gel [eluting first with CHCl₃, then CHCl₃ (1 L w/ 8 drops conc ammonia), then 5% MeOH in CHCl₃ (1 L w/ 8 drops conc. ammonia), then finally with 5% MeOH in CHCl₃ (5 L w/ 40 drops conc ammonia)]. The product was isolated (5.6 g) as a tan waxy solid in 58% yield. ¹H NMR (CDCl₃ ) δ 7.32 (dd, 1H); 7.09–7.01 (m, 2H); 6.81 (t, 1H); 3.92 (br s, 2H); 3.36 (s, 2H); 2.25 (s, 6H).

Part C: Preparation of 1-(3'-Cyano-4'-fluorophenyl)-3-trifluoromethyl-N-[2-fluoro-4-[(2'-dimethylaminomethyl) imidazol-1-yl]phenyl]-1H-pyrazole-5-carboxyamide A suspension of the acid from Example A (38.31 g, 0.128 mol) in 1 L of dichloromethane was added oxalyl chloride (32.5 g, 0.256 mol) and DMF (0.5 mL). The mixture was stirred at rt for 1 h and then refluxed for 1 h. The solvent and excess reagent in the solution were evaporated to give the acid chloride as a yellow solid. The solid was dissolved in 1 L of dichloromethane and cooled with an ice bath. To this was added 2-fluoro-4-[(2-dimethylaminomethyl)-imidazol-1-yl]-aniline (30 g, 0.128 mol) and dimethylaminopyridine (31.3 g, 0.256 mol). The solution was stirred at ambient temperature overnight. The solution was washed with water (3×200 mL), brine (200 mL), dried ($Na_2SO_4$) and concentrated. Column chromatography (silica gel, 0–5 % MeOH/$CH_2Cl_2$) gave 56.1 g (85% yield) of the desired product. $^1$H NMR ($CDCl_3$) δ 8.27 (t, 1H), 8.17 (br, 1H), 7.86–7.79 (m, 2H), 7.74 (dd, 1H), 7.40–7.34 (m, 2H), 7.20 (s, 1H), 7.10–7.08 (m, 2H), 3.37 (s, 2H), 2.26 (s, 6H). MS 561.2 $(M+H)^+$.

Part D: Preparation of 1-(3'-Aminobenzisoxazol-5'-yl)-3-trifluoromethyl-N-[2-fluoro-4-[(2'-dimethylaminomethyl) imidazol-1-yl]phenyl]-1H-pyrazole-5-carboxyamide Into a 2 L flask with mechanical stirrer was added potassium t-butoxide (19.5 g, 0.157 mol), acetohydroxamic acid (11.77 g, 0.157 mol) and 500 mL of DMF. This mixture rapidly produced a thick white precipitate. After 40 minutes, the product from Part C (26.93 g, 0.052 mol) was added all at once as a solid. The mixture turned brown and became very fluid. Stirring was continued at room temperature overnight. The mixture was poured into a separatory funnel containing 500 mL of aqueous ammonium chloride and 500 mL of ethyl acetate. After shaking, the lower aqueous phase separated rapidly. This was drawn off and the organic phase washed again with 500 mL of water. A solid formed at the interface which was filtered off, weighed 8 g. After filtering and evaporating to 100 mL, another 5.5 g of solid precipitated. The first aqueous washing was extracted again with 500 mL of ethyl acetate. This was washed with 400 mL of water, then evaporated down to 75 mL. Another 6 g of solid was collected. The second aqueous washing was extracted again with 500 mL of ethyl acetate. This was washed with 400 mL water then evaporated down to 75 mL. Another 2 g solid was collected. All fractions were combined to give 23.6 g (86 % yield) of the desired product. $^1$H NMR (DMSO-$d_6$) δ 8.10 (d, 1H), 7.73–7.68 (m, 4H), 7.59 (d, 1H), 7.49 (d, 1H) 7.46 (d, 1H), 7.00 (d, 1H), 6.59 (s, 2H), 3.34 (s, 2H), 2.13 (s, 6H). MS $(ES^+)$ 529.2 $(M+H)^+$.

Part E: Preparation of N-[4-(2-[Dimethylaminomethyl]-1H-imidazol-1-yl)-2-fluorophenyl]-1-(3-amidino-4-hydroxyphenyl)-3-(trifluoromethyl)-1H-pyrazole-5-carboxamide The product from Part D (57 mg) was hydrogenated with 10% Pd/C (5mg) and methanol (20 mL) at 35 psi for 30 minutes. The mixture was filtered through Celite®, concentrated, and dried to give 33.5 mg of the desired product. $^1$H NMR (MeOH-$d_4$) δ 7.94 (t, 1H), 7.81 (d, 1H), 7.64 (dd, 1H), 7.40 (d, 1H) 7.34 (d, 3H), 7.06 (s, 1H), 6.75 (d, 1H), 3.45 (s, 2H), 2.20 (s, 6H). MS$(ES^+)$ 531.1 $(M+H)^+$.

UTILITY

The compounds of this invention are inhibitors of factor Xa and are useful as anticoagulants for the treatment or prevention of thromboembolic disorders in mammals (i.e., factor Xa-associated disorders). In general, a thromboembolic disorder is a circulatory disease caused by blood clots (i.e., diseases involving fibrin formation, platelet activation, and/or platelet aggregation). The term "thromboembolic disorders" as used herein includes arterial cardiovascular thromboembolic disorders, venous cardiovascular thromboembolic disorders, and thromboembolic disorders in the chambers of the heart. The term "thromboembolic disorders" as used herein also includes specific disorders selected from, but not limited to, unstable angina or other acute coronary syndromes, first or recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hemodialysis, or (f) other procedures in which blood is exposed to an artificial surface that promotes thrombosis. It is noted that thrombosis includes occlusion (e.g. after a bypass) and reocclusion (e.g., during or after percutaneous transluminal coronary angioplasty). The thromboembolic disorders may result from conditions including but not limited to atherosclerosis, surgery or surgical complications, prolonged immobilization, arterial fibrillation, congenital thrombophilia, cancer, diabetes, effects of medications or hormones, and complications of pregnancy. The anticoagulant effect of compounds of the present invention is believed to be due to inhibition of factor Xa or thrombin.

The effectiveness of compounds of the present invention as inhibitors of factor Xa was determined using purified human factor Xa and synthetic substrate. The rate of factor Xa hydrolysis of chromogenic substrate S2222 (Diapharma/Chromogenix, West Chester, Ohio) was measured both in the absence and presence of compounds of the present invention. Hydrolysis of the substrate resulted in the release of pNA, which was monitored spectrophotometrically by measuring the increase in absorbance at 405 nM. A decrease in the rate of absorbance change at 405 nm in the presence of inhibitor is indicative of enzyme inhibition. The results of this assay are expressed as inhibitory constant, $K_i$.

Factor Xa determinations were made in 0.10 M sodium phosphate buffer, pH 7.5, containing 0.20 M NaCl, and 0.5% PEG 8000. The Michaelis constant, $K_m$, for substrate hydrolysis was determined at 25° C. using the method of Lineweaver and Burk. Values of $K_i$ were determined by allowing 0.2–0.5 nM human factor Xa (Enzyme Research Laboratories, South Bend, Ind.) to react with the substrate (0.20 mM–1 mM) in the presence of inhibitor. Reactions were allowed to go for 30 minutes and the velocities (rate of absorbance change vs time) were measured in the time frame of 25–30 minutes. The following relationship was used to calculate $K_i$ values:

$$(v_o-v_s)/v_s=I/(K_i(1+S/Km))$$

where:

$v_o$ is the velocity of the control in the absence of inhibitor;

$v_s$ is the velocity in the presence of inhibitor;

I is the concentration of inhibitor;

$K_i$ is the dissociation constant of the enzyme:inhibitor complex;

S is the concentration of substrate;

$K_m$ is the Michaelis constant.

Compounds tested in the above assay are considered to be active if they exhibit a $K_i$ of <10 μM. Preferred compounds of the present invention have $K_i$'s of <1 μM. More preferred compounds of the present invention have $K_i$'s of <0.1 μM. Even more preferred compounds of the present invention have $K_i$'s of <0.01 μM. Still more preferred compounds of the present invention have $K_i$'s of <0.001 μM. Using the methodology described above, a number of compounds of the present invention were found to exhibit $K_i$'s of <10 μM, thereby confirming the utility of the compounds of the present invention as effective Xa inhibitors.

The antithrombotic effect of compounds of the present invention can be demonstrated in a rabbit arterio-venous (AV) shunt thrombosis model. In this model, rabbits weighing 2–3 kg anesthetized with a mixture of xylazine (10 mg/kg i.m.) and ketamine (50 mg/kg i.m.) are used. A saline-filled AV shunt device is connected between the femoral arterial and the femoral venous cannulae. The AV shunt device consists of a piece of 6-cm tygon tubing that contains a piece of silk thread. Blood will flow from the femoral artery via the AV-shunt into the femoral vein. The exposure of flowing blood to a silk thread will induce the formation of a significant thrombus. After forty minutes, the shunt is disconnected and the silk thread covered with thrombus is weighed. Test agents or vehicle will be given (i.v., i.p., s.c., or orally) prior to the opening of the AV shunt. The percentage inhibition of thrombus formation is determined for each treatment group. The $ID_{50}$ values (dose which produces 50% inhibition of thrombus formation) are estimated by linear regression.

The compounds of the present invention may also be useful as inhibitors of serine proteases, notably human thrombin, Factor VIIa, Factor IXa, Factor XIa, urokinase, plasma kallikrein and plasmin. Because of their inhibitory action, these compounds are indicated for use in the prevention or treatment of physiological reactions, blood coagulation and inflammation, catalyzed by the aforesaid class of enzymes. Specifically, the compounds have utility as drugs for the treatment of diseases arising from elevated thrombin activity such as myocardial infarction, and as reagents used as anticoagulants in the processing of blood to plasma for diagnostic and other commercial purposes.

Some compounds of the present invention were shown to be direct acting inhibitors of the serine protease thrombin by their ability to inhibit the cleavage of small molecule substrates by thrombin in a purified system. In vitro inhibition constants were determined by the method described by Kettner et al. in *J. Biol. Chem.* 265, 18289–18297 (1990), herein incorporated by reference. In these assays, thrombin-mediated hydrolysis of the chromogenic substrate S2238 (Helena Laboratories, Beaumont, Tex.) was monitored spectrophotometrically. Addition of an inhibitor to the assay mixture results in decreased absorbance and is indicative of thrombin inhibition. Human thrombin (Enzyme Research Laboratories, Inc., South Bend, Ind.) at a concentration of 0.2 nM in 0.10 M sodium phosphate buffer, pH 7.5, 0.20 M NaCl, and 0.5% PEG 6000, was incubated with various substrate concentrations ranging from 0.20 to 0.02 mM. After 25 to 30 minutes of incubation, thrombin activity was assayed by monitoring the rate of increase in absorbance at 405 nm that arises owing to substrate hydrolysis. Inhibition constants were derived from reciprocal plots of the reaction velocity as a function of substrate concentration using the standard method of Lineweaver and Burk. Using the methodology described above, some compounds of this invention were evaluated and found to exhibit a $K_i$ of less than 10 μm, thereby confirming the utility of the compounds of the present invention as effective thrombin inhibitors.

The compounds of the present invention can be administered alone or in combination with one or more additional therapeutic agents. These include other anti-coagulant or coagulation inhibitory agents, anti-platelet or platelet inhibitory agents, thrombin inhibitors, or thrombolytic or fibrinolytic agents.

The compounds are administered to a mammal in a therapeutically effective amount. By "therapeutically effective amount" it is meant an amount of a compound of the present invention that, when administered alone or in combination with an additional therapeutic agent to a mammal, is effective to prevent or ameliorate the thromboembolic disease condition or the progression of the disease.

By "administered in combination" or "combination therapy" it is meant that a compound of the present invention and one or more additional therapeutic agents are administered concurrently to the mammal being treated. When administered in combination each component may be administered at the same time or sequentially in any order at different points in time. Thus, each component may be administered separately but sufficiently closely in time so as to provide the desired therapeutic effect. Other anticoagulant agents (or coagulation inhibitory agents) that may be used in combination with the compounds of this invention include warfarin and heparin (either unfractionated heparin or any commercially available low molecular weight heparin), synthetic pentasaccharide, direct acting thrombin inhibitors including hirudin and argatrobanas well as other factor Xa inhibitors such as those described in the publications identified above under Background of the Invention.

The term anti-platelet agents (or platelet inhibitory agents), as used herein, denotes agents that inhibit platelet function, for example by inhibiting the aggregation, adhesion or granular secretion of platelets. Agents include, but are not limited to, the various known non-steroidal anti-inflammatory drugs (NSAIDS) such as aspirin, ibuprofen, naproxen, sulindac, indomethacin, mefenamate, droxicam, diclofenac, sulfinpyrazone, piroxicam, and pharmaceutically acceptable salts or prodrugs thereof. Of the NSAIDS, aspirin (acetylsalicyclic acid or ASA) and piroxicam are preferred. Other suitable platelet inhibitory agents include IIb/IIIa antagonists (e.g., tirofiban, eptifibatide, and abciximab), thromboxane-A2-receptor antagonists (e.g., ifetroban), thromboxane-A2-synthetase inhibitors, PDE-III inhibitors (e.g., dipyridamole), and pharmaceutically acceptable salts or prodrugs thereof.

The term anti-platelet agents (or platelet inhibitory agents), as used herein, is also intended to include ADP (adenosine diphosphate) receptor antagonists, preferably antagonists of the purinergic receptors $P_2Y_1$ and $P_2Y_{12}$, with $P_2Y_{12}$ being even more preferred. Preferred $P_2Y_{12}$ receptor antagonists include ticlopidine and clopidogrel, including pharmaceutically acceptable salts or prodrugs thereof. Clopidogrel is an even more preferred agent. Ticlopidine and clopidogrel are also preferred compounds since they are known to be gentle on the gastro-intestinal tract in use.

The term thrombin inhibitors (or anti-thrombin agents), as used herein, denotes inhibitors of the serine protease thrombin. By inhibiting thrombin, various thrombin-mediated processes, such as thrombin-mediated platelet activation (that is, for example, the aggregation of platelets, and/or the granular secretion of plasminogen activator inhibitor-1 and/or serotonin) and/or fibrin formation are disrupted. A number of thrombin inhibitors are known to one of skill in the art and these inhibitors are contemplated to be used in combination with the present compounds. Such inhibitors include, but are not limited to, boroarginine derivatives, boropeptides, heparins, hirudin, argatroban, and melagatran, including pharmaceutically acceptable salts and prodrugs thereof. Boroarginine derivatives and boropeptides include N-acetyl and peptide derivatives of boronic acid, such as C-terminal α-aminoboronic acid derivatives of lysine, ornithine, arginine, homoarginine and corresponding isothiouronium analogs thereof. The term hirudin, as used herein, includes suitable derivatives or analogs of hirudin, referred to herein as hirulogs, such as disulfatohirudin.

The term thrombolytics or fibrinolytic agents (or thrombolytics or fibrinolytics), as used herein, denote agents that lyse blood clots (thrombi). Such agents include tissue plasminogen activator (natural or recombinant) and modified forms thereof, anistreplase, urokinase, streptokinase, tenecteplase (TNK), lanoteplase (nPA), factor VIIa inhibitors, PAI-1 inhibitors (i.e., inactivators of tissue plasminogen activator inhibitors), alpha2-antiplasmin inhibitors, and anisoylated plasminogen streptokinase activator complex, including pharmaceutically acceptable salts or prodrugs thereof. The term anistreplase, as used herein, refers to anisoylated plasminogen streptokinase activator complex, as described, for example, in EP 028,489, the disclosure of which is hereby incorporated herein by reference herein. The term urokinase, as used herein, is intended to denote both dual and single chain urokinase, the latter also being referred to herein as prourokinase.

Examples of suitable anti-arrythmic agents for use in combination with the present compounds include: Class I agents (such as propafenone); Class II agents (such as carvadiol and propranolol); Class III agents (such as sotalol, dofetilide, amiodarone, azimilide and ibutilide); Class IV agents (such as ditiazem and verapamil); K$^+$ channel openers such as $I_{Ach}$ inhibitors, and $I_{Kur}$ inhibitors (e.g., compounds such as those disclosed in WO01/40231).

Examples of suitable anti-hypertensive agents for use in combination with the compounds of the present invention include: alpha adrenergic blockers; beta adrenergic blockers; calcium channel blockers (e.g., diltiazem, verapamil, nifedipine, amlodipine and mybefradil); diruetics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, spironolactone); renin inhibitors; ACE inhibitors (e.g., captopril, zofenopril, fosinopril, enalapril, ceranopril, cilazopril, delapril, pentopril, quinapril, ramipril, lisinopril); AT-1 receptor antagonists (e.g., losartan, irbesartan, valsartan); ET receptor antagonists (e.g., sitaxsentan, atrsentan and compounds disclosed in U.S. Pat. Nos. 5,612,359 and 6,043,265); Dual ET/AII antagonist (e.g., compounds disclosed in WO 00/01389); neutral endopeptidase (NEP) inhibitors; vasopepsidase inhibitors (dual NEP-ACE inhibitors) (e.g., omapatrilat, gemopatrilat and nitrates).

Examples of suitable calcium channel blockers (L-type or T-type) for use in combination with the compounds of the present invention include diltiazem, verapamil, nifedipine, amlodipine and mybefradil.

Examples of suitable cardiac glycosides for use in combination with the compounds of the present invention include digitalis and ouabain.

Examples of suitable diruetics for use in combination with the compounds of the present invention include: chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimine, bumetanide, triamtrenene, amiloride, and spironolactone.

Examples of suitable mineralocorticoid receptor antagonists for use in combination with the compounds of the present invention include sprionolactone and eplirinone.

Examples of suitable phospodiesterase inhibitors for use in combination with the compounds of the present invention include: PDE III inhibitors (such as cilostazol); and PDE V inhibitors (such as sildenafil).

Examples of suitable cholesterol/lipid lowering agents and lipid profile therapies for use in combination with the compounds of the present invention include: HMG-CoA reductase inhibitors (e.g., pravastatin, lovastatin, atorvastatin, simvastatin, fluvastatin, NK-104 (a.k.a. itavastatin, or nisvastatin or nisbastatin) and ZD-4522 (a.k.a. rosuvastatin, or atavastatin or visastatin)); squalene synthetase inhibitors; fibrates; bile acid sequestrants (such as questran); ACAT inhibitors; MTP inhibitors; lipooxygenase inhibitors; choesterol absorption inhibitors; and cholesterol ester transfer protein inhibitors (e.g., CP-529414).

Examples of suitable anti-diabetic agents for use in combination with the compounds of the present invention include: biguanides (e.g., metformin); glucosidase inhibitors (e.g., acarbose); insulins (including insulin secretagogues or insulin sensitizers); meglitinides (e.g., repaglinide); sulfonylureas (e.g., glimepiride, glyburide and glipizide); biguanide/glyburide combinations (e.g., glucovance), thiozolidinediones (e.g., troglitazone, rosiglitazone and pioglitazone), PPAR-alpha agonists, PPAR-gamma agonists, PPAR alpha/gamma dual agonists, SGLT2 inhibitors, inhibitors of fatty acid binding protein (aP2) such as those disclosed in WO00/59506, glucagon-like peptide-1 (GLP-1), and dipeptidyl peptidase IV (DP4) inhibitors.

Examples of suitable anti-depressant agents for use in combination with the compounds of the present invention include nefazodone and sertraline.

Examples of suitable anti-inflammatory agents for use in combination with the compounds of the present invention include: prednisone; dexamethasone; enbrel; protien tyrosine kinase (PTK) inhibitors; cyclooxygenase inhibitors (including NSAIDs, and COX-1 and/or COX-2 inhibitors); aspirin; indomethacin; ibuprofen; prioxicam; naproxen; celecoxib; and/or rofecoxib.

Examples of suitable anti-osteoporosis agents for use in combination with the compounds of the present invention include alendronate and raloxifene.

Examples of suitable hormone replacement therapies for use in combination with the compounds of the present invention include estrogen (e.g., congugated estrogens) and estradiol.

Examples of suitable anti-coagulants for use in combination with the compounds of the present invention include heparins (e.g., unfractioned and low molecular weight heparins such as enoxaparin and dalteparin).

Examples of suitable anti-obesity agents for use in combination with the compounds of the present invention include orlistat and aP2 inhibitors (such as those disclosed in WO00/59506).

Examples of suitable anti-anxiety agents for use in combination with the compounds of the present invention include diazepam, lorazepam, buspirone, and hydroxyzine pamoate.

Examples of suitable anti-proliferative agents for use in combination with the compounds of the present invention include cyclosporin A, paclitaxel, adriamycin; epithilones, cisplatin, and carboplatin.

Examples of suitable anti-ulcer and gastroesophageal reflux disease agents for use in combination with the compounds of the present invention include famotidine, ranitidine, and omeprazole.

Administration of the compounds of the present invention (i.e., a first therapeutic agent) in combination with at least one additional therapeutic agent (i.e., a second therapeutic agent), preferably affords an efficacy advantage over the compounds and agents alone, preferably while permitting the use of lower doses of each (i.e., a synergistic combination). A lower dosage minimizes the potential of side effects, thereby providing an increased margin of safety. It is preferred that at least one of the therapeutic agents is administered in a sub-therapeutic dose. It is even more preferred that all of the therapeutic agents be administered in sub-therapeutic doses. Sub-therapeutic is intended to mean an amount of a therapeutic agent that by itself does not give the desired therapeutic effect for the condition or disease being treated. Synergistic combination is intended to mean that the observed effect of the combination is greater than the sum of the individual agents administered alone.

The compounds of the present invention are also useful as standard or reference compounds, for example as a quality standard or control, in tests or assays involving the inhibition of factor Xa. Such compounds may be provided in a commercial kit, for example, for use in pharmaceutical research involving factor Xa. For example, a compound of the present invention could be used as a reference in an assay to compare its known activity to a compound with an unknown activity. This would ensure the experimenter that the assay was being performed properly and provide a basis for comparison, especially if the test compound was a derivative of the reference compound. When developing new assays or protocols, compounds according to the present invention could be used to test their effectiveness.

The compounds of the present invention may also be used in diagnostic assays involving factor Xa. For example, the presence of factor Xa in an unknown sample could be determined by addition of chromogenic substrate S2222 to a series of solutions containing test sample and optionally one of the compounds of the present invention. If production of pNA is observed in the solutions containing test sample, but not in the presence of a compound of the present invention, then one would conclude factor Xa was present.

The present invention also encompasses an article of manufacture. As used herein, article of manufacture is intended to include, but not be limited to, kits and packages. The article of manufacture of the present invention, comprises: (a) a first container; (b) a pharmaceutical composition located within the first container, wherein the composition, comprises: a first therapeutic agent, comprising: a compound of the present invention or a pharmaceutically acceptable salt form thereof; and, (c) a package insert stating that the pharmaceutical composition can be used for the treatment of a thromboembolic disorder (as defined previously). In another embodiment, the package insert states that the pharmaceutical composition can be used in combination (as defined previously) with a second therapeutic agent to treat a thromboembolic disorder. The article of manufacture can further comprise: (d) a second container, wherein components (a) and (b) are located within the second container and component (c) is located within or outside of the second container. Located within the first and second containers means that the respective container holds the item within its boundaries.

The first container is a receptacle used to hold a pharmaceutical composition. This container can be for manufacturing, storing, shipping, and/or individual/bulk selling. First container is intended to cover a bottle, jar, vial, flask, syringe, tube (e.g., for a cream preparation), or any other container used to manufacture, hold, store, or distribute a pharmaceutical product.

The second container is one used to hold the first container and, optionally, the package insert. Examples of the second container include, but are not limited to, boxes (e.g., cardboard or plastic), crates, cartons, bags (e.g., paper or plastic bags), pouches, and sacks. The package insert can be physically attached to the outside of the first container via tape, glue, staple, or another method of attachment, or it can rest inside the second container without any physical means of attachment to the first container. Alternatively, the package insert is located on the outside of the second container. When located on the outside of the second container, it is preferable that the package insert is physically attached via tape, glue, staple, or another method of attachment. Alternatively, it can be adjacent to or touching the outside of the second container without being physically attached.

The package insert is a label, tag, marker, etc. that recites information relating to the pharmaceutical composition located within the first container. The information recited will usually be determined by the regulatory agency governing the area in which the article of manufacture is to be sold (e.g., the United States Food and Drug Administration). Preferably, the package insert specifically recites the indications for which the pharmaceutical composition has been approved. The package insert may be made of any material on which a person can read information contained therein or thereon. Preferably, the package insert is a printable material (e.g., paper, plastic, cardboard, foil, adhesive-backed paper or plastic, etc.) on which the desired information has been formed (e.g., printed or applied).

Dosage and Formulation

The compounds of this invention can be administered in such oral dosage forms as tablets, capsules (each of which includes sustained release or timed release formulations), pills, powders, granules, elixirs, tinctures, suspensions, syrups, and emulsions. They may also be administered in intravenous (bolus or infusion), intraperitoneal, subcutaneous, or intramuscular form, all using dosage forms well known to those of ordinary skill in the pharmaceutical arts. They can be administered alone, but generally will be administered with a pharmaceutical carrier selected on the basis of the chosen route of administration and standard pharmaceutical practice.

The dosage regimen for the compounds of the present invention will, of course, vary depending upon known factors, such as the pharmacodynamic characteristics of the particular agent and its mode and route of administration; the species, age, sex, health, medical condition, and weight of the recipient; the nature and extent of the symptoms; the kind of concurrent treatment; the frequency of treatment; the route of administration, the renal and hepatic function of the patient, and the effect desired. A physician or veterinarian can determine and prescribe the effective amount of the drug required to prevent, counter, or arrest the progress of the thromboembolic disorder.

By way of general guidance, the daily oral dosage of each active ingredient, when used for the indicated effects, will range between about 0.001 to 1000 mg/kg of body weight, preferably between about 0.01 to 100 mg/kg of body weight per day, and most preferably between about 1.0 to 20 mg/kg/day. Intravenously, the most preferred doses will range from about 1 to about 10 mg/kg/minute during a constant rate infusion. Compounds of this invention may be administered in a single daily dose, or the total daily dosage may be administered in divided doses of two, three, or four times daily.

Compounds of this invention can be administered in intranasal form via topical use of suitable intranasal vehicles, or via transdermal routes, using transdermal skin patches. When administered in the form of a transdermal delivery system, the dosage administration will, of course, be continuous rather than intermittent throughout the dosage regimen.

The compounds are typically administered in admixture with suitable pharmaceutical diluents, excipients, or carriers (collectively referred to herein as pharmaceutical carriers) suitably selected with respect to the intended form of administration, that is, oral tablets, capsules, elixirs, syrups and the like, and consistent with conventional pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

The compounds of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine, or phosphatidylcholines.

Compounds of the present invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxide-polylysine substituted with palmitoyl residues. Furthermore, the compounds of the present invention may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacylates, and crosslinked or amphipathic block copolymers of hydrogels.

Dosage forms (pharmaceutical compositions) suitable for administration may contain from about 1 milligram to about 100 milligrams of active ingredient per dosage unit. In these pharmaceutical compositions the active ingredient will ordinarily be present in an amount of about 0.5–95% by weight based on the total weight of the composition.

Gelatin capsules may contain the active ingredient and powdered carriers, such as lactose, starch, cellulose derivatives, magnesium stearate, stearic acid, and the like. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract.

Liquid dosage forms for oral administration can contain coloring and flavoring to increase patient acceptance.

In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl-or propyl-paraben, and chlorobutanol.

Suitable pharmaceutical carriers are described in *Remington's Pharmaceutical Sciences*, 18th ed., Mack Publishing Company, Easton, Pa., 1990, a standard reference text in this field.

Where the compounds of this invention are combined with other anticoagulant agents, for example, a daily dosage may be about 0.1 to 100 milligrams of the compound of Formula I and about 1 to 7.5 milligrams of the second anticoagulant, per kilogram of patient body weight. For a tablet dosage form, the compounds of this invention generally may be present in an amount of about 5 to 10 milligrams per dosage unit, and the second anti-coagulant in an amount of about 1 to 5 milligrams per dosage unit.

Where the compounds of the present invention are administered in combination with an anti-platelet agent, by way of general guidance, typically a daily dosage may be about 0.01 to 25 milligrams of the compound of Formula I and about 50 to 150 milligrams of the anti-platelet agent, preferably about 0.1 to 1 milligrams of the compound of Formula I and about 1 to 3 milligrams of antiplatelet agents, per kilogram of patient body weight.

Where the compounds of Formula I are administered in combination with thrombolytic agent, typically a daily dosage may be about 0.1 to 1 milligrams of the compound of Formula I, per kilogram of patient body weight and, in the case of the thrombolytic agents, the usual dosage of the thrombolyic agent when administered alone may be reduced by about 70–80% when administered with a compound of Formula I.

Where two or more of the foregoing second therapeutic agents are administered with the compound of Formula I, generally the amount of each component in a typical daily dosage and typical dosage form may be reduced relative to the usual dosage of the agent when administered alone, in view of the additive or synergistic effect of the therapeutic agents when administered in combination.

Particularly when provided as a single dosage unit, the potential exists for a chemical interaction between the combined active ingredients. For this reason, when the compound of Formula I and a second therapeutic agent are combined in a single dosage unit they are formulated such that although the active ingredients are combined in a single dosage unit, the physical contact between the active ingredients is minimized (that is, reduced). For example, one active ingredient may be enteric coated. By enteric coating one of the active ingredients, it is possible not only to minimize the contact between the combined active ingredients, but also, it is possible to control the release of one of these components in the gastrointestinal tract such that one of these components is not released in the stomach but ratheR is released in the intestines. One of the active ingredients may also be coated with a material that affects a sustained-release throughout the gastrointestinal tract and also serves to minimize physical contact between the combined active ingredients. Furthermore, the sustained-released component can be additionally enteric coated such that the release of this component occurs only in the intestine. Still another approach would involve the formulation of a combination product in which the one component is coated with a sustained and/or enteric release polymer, and the other component is also coated with a polymer such as a low-viscosity grade of hydroxypropyl methylcellulose (HPMC) or other appropriate materials as known in the art, in order to further separate the active components. The polymer coating serves to form an additional barrier to interaction with the other component.

These as well as other ways of minimizing contact between the components of combination products of the present invention, whether administered in a single dosage form or administered in separate forms but at the same time by the same manner, will be readily apparent to those skilled in the art, once armed with the present disclosure.

Numerous modifications and variations of the present invention are possible in light of the above teachings. It is therefore to be understood that within the scope of the appended claims, the invention may be practiced otherwise that as specifically described herein.

What is claimed is:

1. A compound of formula I:

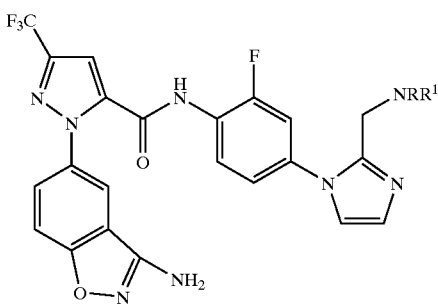

I or a pharmaceutically acceptable salt thereof, wherein:
R is $CH_3$ and $R^1$ is H.

2. A compound of formula I:

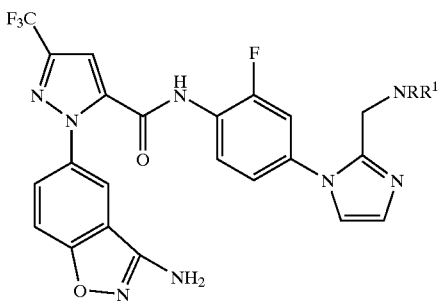

I or a pharmnaceutically acceptable salt thereof, wherein:
R is H and $R^1$ is H.

3. A pharmaceutical composition, comprising: a pharmaceutically acceptable carrier and a therapeutically effective amount of a compound according to claim 1 or a pharmaceutically acceptable salt thereof.

4. A pharmaceutical composition, comprising; a pharmaceutically acceptable carrier and a therapeutically effective amount of a compound according to claim 2 or a pharmaceutically acceptable salt thereof.

5. A method for treating a thromboembolic disorder, comprising: administering to a patient in need thereof a therapeutically effective amount of a compound of claim 1 or a pharmaceutically acceptable salt form thereof.

6. A method according to claim 2, wherein the thromboembolic disorder is selected from the group consisting of arterial cardiovascular thromboembolic disorders, venous cardiovascular thromboembolic disorders, and thromboembolic disorders in the chambers of the heart.

7. A method according to claim 6, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmnonary bypass, (e) hemodialysis, or (f) other procedures in which blood is exposed to an artificial surface that promotes thrombosis.

8. A method for treating a thromboembolic disorder, comprising: administering to a patient in need thereof a therapeutically effective amount of a compound of claim 2 or a pharmaceutically acceptable salt form thereof.

9. A method according to claim 8, wherein the thromboembolic disorder is selected tom the group consisting of arterial cardiovascular thromboembolic disorders, venous cardiovascular thromboembolic disorders, and thromboembolic disorders in the chambers of the heart.

10. A method according to claim 9, wherein the thromboembolic disorder is selected from unstable angina, an acute coronary syndrome, first myocardial infarction, recurrent myocardial infarction, ischemic sudden death, transient ischemic attack, stroke, atherosclerosis, peripheral occlusive arterial disease, venous thrombosis, deep vein thrombosis, thrombophlebitis, arterial embolism, coronary arterial thrombosis, cerebral arterial thrombosis, cerebral embolism, kidney embolism, pulmonary embolism, and thrombosis resulting from (a) prosthetic valves or other implants, (b) indwelling catheters, (c) stents, (d) cardiopulmonary bypass, (e) hernodialysis, or (f) other procedures in which blood is exposed to an artificial surface that promotes thrombosis.

* * * * *